US010925767B2

United States Patent
Miller et al.

(10) Patent No.: US 10,925,767 B2
(45) Date of Patent: Feb. 23, 2021

(54) LASER DOPPLER VIBROMETRY FOR EYE SURFACE VIBRATION MEASUREMENT TO DETERMINE CELL DAMAGE

(71) Applicant: LUTRONIC VISION INC., Burlington, MA (US)

(72) Inventors: Seth Adrian Miller, Longmont, CO (US); Mark Meloni, Longmont, CO (US)

(73) Assignee: LUTRONIC VISION INC, Burlington, MA (US)

( * ) Notice: Subject to any disclaimer, the term of this patent is extended or adjusted under 35 U.S.C. 154(b) by 0 days.

(21) Appl. No.: 16/975,162

(22) PCT Filed: Mar. 6, 2018

(86) PCT No.: PCT/US2018/021184
§ 371 (c)(1),
(2) Date: Aug. 24, 2020

(87) PCT Pub. No.: WO2019/172894
PCT Pub. Date: Sep. 12, 2019

(65) Prior Publication Data
US 2021/0000645 A1    Jan. 7, 2021

(51) Int. Cl.
*A61F 9/008* (2006.01)
*G01B 9/02* (2006.01)
(Continued)

(52) U.S. Cl.
CPC .......... *A61F 9/008* (2013.01); *G01B 9/02084* (2013.01); *G01H 9/00* (2013.01);
(Continued)

(58) Field of Classification Search
CPC .................................. G01H 9/00; B06B 1/02
See application file for complete search history.

(56) References Cited

U.S. PATENT DOCUMENTS

| 4,834,111 A | 5/1989 | Khanna et al. |
| 5,347,327 A | 9/1994 | Sekine et al. |

(Continued)

FOREIGN PATENT DOCUMENTS

WO    2014170556 A1    10/2014

OTHER PUBLICATIONS

"Basic Principles of Vibrometry," Polytec, accessed at https://web.archive.org/web/20170713072918/http://www.polytec.com/us/solutions/vibration-measurement/basic-principles-of-vibrometry/, archived at Jul. 13, 2017, accessed at Nov. 30, 2017, pp. 3.

(Continued)

*Primary Examiner* — Scott Luan

(57) ABSTRACT

Technologies are described for detection of eye surface vibrations to determine cell damage within a treatment area of an eye undergoing laser treatment. Eye surface vibrations may be caused by intraocular pressure waves that form during the laser treatment. For example, the pressure waves may originate from a plurality of bubbles forming and/or rupturing inside cells located in the treatment area. The bubbles may form as energy from a treatment laser beam is absorbed by the retinal tissue. The pressure waves may be measured at the surface of the eye through Doppler vibrometry to determine if the cells within the treatment area have been damaged. The damage to the cells may include cell lysis, a rupture of cell membranes, scarring, and/or photocoagulation, among other examples.

20 Claims, 8 Drawing Sheets

(51) Int. Cl.
  *G01H 9/00* (2006.01)
  *A61B 90/00* (2016.01)
  *A61B 17/00* (2006.01)

(52) U.S. Cl.
  CPC ............. *A61B 2017/00057* (2013.01); *A61B 2017/00123* (2013.01); *A61B 2017/00221* (2013.01); *A61B 2090/049* (2016.02); *A61B 2090/0409* (2016.02); *A61F 9/00821* (2013.01); *A61F 2009/00844* (2013.01)

(56) References Cited

U.S. PATENT DOCUMENTS

2006/0077395 A1  4/2006  Chan et al.
2017/0258332 A1  9/2017  Wynn et al.

OTHER PUBLICATIONS

International Search Report and Written Opinion for International Application No. PCT/US2018/021184 dated May 14, 2018, pp. 10.

Carter, S., et al., "Selecting Piezoresistive vs. Piezoelectric Pressure Transducers," Kulite Semiconductor Products, Inc., pp. 1-25 (Dec. 5, 2014)

Fukushima, Y., et al., "A performance study of a laser doppler vibrometer for measuring waveforms from piezoelectric transducers," IEEE Transactions on Ultrasonics Ferroelectrics and Frequency Control, vol. 56, No. 07, pp. 1442-1450 (Jul. 2009).

Herdier, R., et al., "Laser Doppler vibrometry for evaluating the piezoelectric coefficient d 33 on thin film," Review of scientific Instruments, vol. 77, Issue No. 9, pp. 093905-093905-5 (Oct. 2006).

Hsu, Y-C., et al.,"Demonstration and characterization of PZT thin-film sensors and actuators for meso- and micro-structures," Sensors and Actuators A: Physical, vol. 116, No. 3, pp. 369-377 (Oct. 2004).

Johansmann, M., et al., "Targeting the Limits of Laser Doppler Vibrometry," All Polytec, pp. 1-12 (2005).

Neumann, J., and Brinkmann, R., "Interferometric noncontact on-line dosimetry control during selective retina treatment (SRT)," Proceedings of SPIE—The International Society for Optical Engineering, vol. 5695, pp. 340-347 (Apr. 2005).

Salman, M., "Continuous Scanning Laser Doppler Vibrometry for Synchronized Array Measurements: Applications to Non-Contact Sensing of Human Body Vibrations," Georgia Institute of Technology, pp. 92 (Dec. 2012).

Scalise, L., et al., "Self-mixing laser diode velocimetry: application to vibration and velocity measurement," IEEE Transactions on Instrumentation and Measurement, vol. 53, Issue No. 1, pp. 223-232 (Feb. 2004).

Traynor, R., "Non-Contact Vibration Measurement of Micro-Structures," Laser Vibrometer Specialist at Lambda Photometrics, pp. 26 (Apr. 14, 2003).

COMPUTER PROGRAM PRODUCT 800

SIGNAL BEARING MEDIUM 802

804 ONE OR MORE INSTRUCTIONS TO:

RECEIVE A FIRST SIGNAL BASED ON A FIRST BEAM AND A SECOND SIGNAL BASED ON A REFLECTED BEAM FROM A LASER DOPPLER VIBROMETER;
DERIVE A BEAT PATTERN SIGNAL FROM AN INTERFERENCE BETWEEN THE FIRST SIGNAL AND THE SECOND SIGNAL; AND
DETERMINE A DAMAGE TO ONE OR MORE CELLS WITHIN A TREATMENT AREA OF THE EYE BASED ON A FREQUENCY OF THE BEAT PATTERN SIGNAL

| COMPUTER-READABLE MEDIUM 806 | RECORDABLE MEDIUM 808 | COMMUNICATIONS MEDIUM 810 |

FIG. 8

LASER DOPPLER VIBROMETRY FOR EYE SURFACE VIBRATION MEASUREMENT TO DETERMINE CELL DAMAGE

CROSS-REFERENCE TO RELATED APPLICATIONS

The present application is a U.S. National Stage filing under 35 U.S.C. § 371 of International Application PCT/US2018/021184, filed Mar. 6, 2018 and entitled "LASER DOPPLER VIBROMETRY FOR EYE SURFACE VIBRATION MEASUREMENT TO DETERMINE CELL DAMAGE." The International Application, including any appendices or attachments thereof, is incorporated by reference herein in its entirety.

BACKGROUND

Unless otherwise indicated herein, the materials described in this section are not prior art to the claims in this application and are not admitted to be prior art by inclusion in this section.

Current methods for measuring eye surface vibration to determine cell damage typically rely on piezoelectric sensors mounted to the surface of the eye via a contact lens apparatus. The piezoelectric sensor is used to measure intraocular pressure waves at the surface of the eye by measuring the vibrations across the surface area of the contact apparatus. The contact apparatus is commonly large relative to the wavelength of the pressure wave. As the pressure wave moves through the vitreous humor, the pressure wave may reflect off of the retina in one or more locations leading to positive and negative interference with the pressure wave in varying amounts across the surface of the eye. The interference may result in a signal strength of the piezoelectric sensors that may be modestly above the noise level.

SUMMARY

The present disclosure generally describes techniques to measure eye surface vibration through laser Doppler vibrometry to determine cell damage.

According to some examples, a method to determine cell damage within an eye undergoing laser treatment may comprise directing a probe laser beam toward a surface of the eye by splitting the probe laser beam into a first beam and a second beam and directing the second beam toward the surface of the eye. The method may further comprise detecting a beat pattern signal between the first beam and a reflected beam, the reflected beam being the second beam reflected from the surface of the eye, and determining a damage to one or more cells within a treatment area of the eye based on a frequency of the beat pattern signal.

According to other examples, a laser Doppler vibrometer may be comprised of a probe laser source configured to direct a probe laser beam toward a surface of an eye, a beam splitter positioned between the probe laser source and the eye and configured to split the probe laser beam into a first beam and a second beam such that the second beam may be directed toward the surface of the eye, and a detector. The detector may be configured to detect the first beam and a reflected beam, the reflected beam being the second beam reflected from the surface of the eye, and provide a first signal based on the first beam and a second signal based on the reflected beam to a signal processing apparatus, where the signal processing apparatus may be configured to derive a beat pattern signal from an interference between the first signal and the second signal in order to determine a damage to one or more cells within a treatment area of the eye based on a frequency of the beat pattern signal.

According to other examples, a signal processing apparatus may be comprised of a communication interface configured to facilitate communication between the signal processing apparatus and a laser Doppler vibrometer. The laser Doppler vibrometer may be configured to direct a probe laser beam toward a surface of the eye by splitting the probe laser beam into a first beam and a second beam such that the second beam may be directed toward the surface of the eye, and detect the first beam and a reflected beam, the reflected beam being the second beam reflected from the surface of the eye. The signal processing apparatus may also be comprised of a processor coupled to the communication interface. The processor may be configured to receive, from the laser Doppler vibrometer through the communication interface, a first signal based on the first beam and a second signal based on the reflected beam, derive a beat pattern signal from an interference between the first signal and the second signal, and determine a damage to one or more cells within a treatment area of the eye on a frequency of the beat pattern signal.

According to other embodiments, a system to determine cell damage within an eye undergoing laser treatment may be comprised of a laser treatment system configured to direct a treatment laser beam to a treatment area of the eye and a laser Doppler vibrometer communicatively coupled to the treatment system. The laser Doppler vibrometer may be configured to direct a probe laser beam toward a surface of the eye by splitting the probe laser beam into a first beam and a second beam, directing the second beam toward the surface of the eye, and detect the first beam and a reflected beam, the reflected beam being the second beam reflected from the surface of the eye. The system may also comprise a signal processing apparatus communicatively coupled to the laser treatment system and the laser Doppler vibrometer. The signal processing apparatus may be configured to receive a first signal based on the first beam and a second signal based on the reflected beam, derive a beat pattern signal from an interference between the first signal and the second signal, and determine a damage to one or more cells within the treatment area of the eye based on a frequency of the beat pattern signal.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 8 illustrates a block diagram of an example computer program product, some of which are arranged in accordance with at least some embodiments described herein.

DETAILED DESCRIPTION

Figure 1:
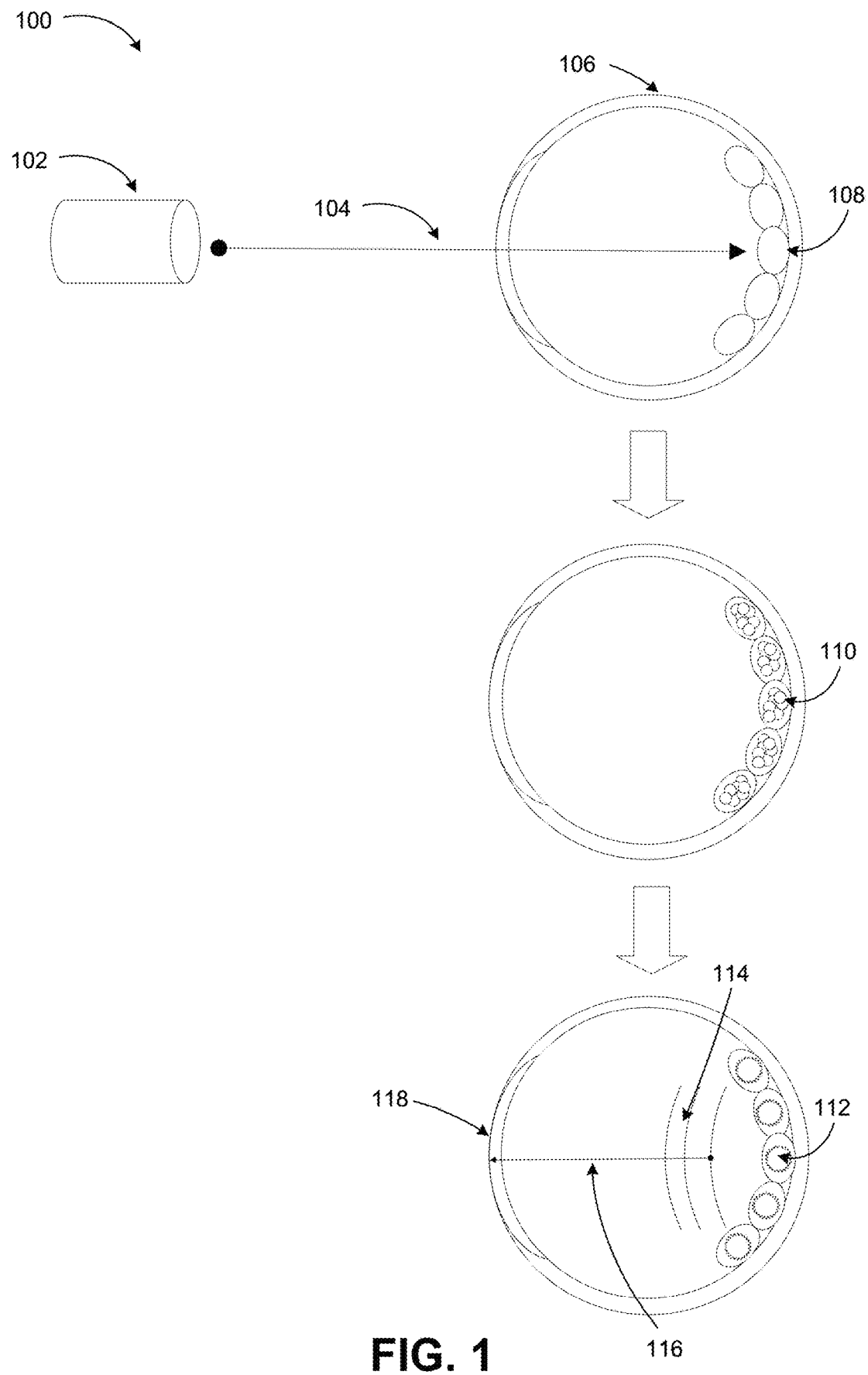
FIG. 1 includes a conceptual illustration of bubble formation events and cell damage in an eye undergoing laser treatment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to measurement of eye surface vibration through laser Doppler vibrometry to determine cell damage in an eye undergoing laser treatment.

Briefly stated, technologies are generally described to measure eye surface vibrations to determine cell damage. Eye surface vibrations may be caused by intraocular pressure waves that form during laser treatment of cells within the eye. The pressure waves may originate from a plurality of bubbles forming and subsequently rupturing at the treatment area. The bubbles may form as energy from a treatment laser beam is absorbed by the retinal tissue. The pressure waves may be measured at the surface of the eye through Doppler vibrometry to determine if cells within the treatment area have been damaged. The damage to the cells may include cell lysis, a rupture of cell membranes, scarring, and/or photocoagulation, among other examples.

FIG. 1 includes a conceptual illustration of bubble formation events and cell damage in an eye undergoing laser treatment.

As shown in diagram 100, a laser source 102 may be configured to generate a treatment laser beam 104. In some examples, the laser source 102 may be a semiconductor laser diode, a super-luminescent laser diode, a chemical laser, a gas laser, a solid-state laser, and/or an optical fiber laser. The treatment laser beam 104 may be directed towards a group of cells 108 inside of an eye 106. In some examples, the group of cells 108 may be located in the macular region of the eye 106. As the group of cells 108 absorb the energy from the treatment laser beam 104, bubbles 110 may begin to form inside the treated cells. Formation of the bubbles 110 may be the result of water inside the cells being vaporized. The bubbles 110 may increase in size during treatment and may continue to grow until they rupture 112. The rupture 112 of the bubbles 110 may cause a pressure wave 114 to form within the vitreous humor 116. The pressure wave 114 may then travel throughout the vitreous humor 116 to the boundaries of the eye 106. The pressure wave 114 may contact the surface of the eye 118 and cause the surface of the eye 118 to vibrate.

In an example scenario, a treatment laser beam may be directed towards a group of cells in the macular region of a patient's eye in order to damage the cells, which may be a source of vision impairment for the patient. The treatment laser beam of a particular intensity may be initiated and subsequently absorbed by the group of cells. After absorbing energy from the treatment laser beam, a plurality of bubbles may form in the cells. These bubbles may originate from water being vaporized within the cell. If treatment continues, bubbles may continue to form and may eventually rupture. The rupturing of these bubbles may cause a pressure wave to form within the eye. The pressure wave may travel to the surface of the patient's eye causing it to vibrate. The vibration of the surface of the eye may then be measured to determine if the group of cells was damaged as intended.

In the conceptual diagram 100, the positioning and structure of the laser source 102, treatment laser beam 104, the eye 106, the group of cells 108, the bubbles 110, the rupture 112 of the bubbles 110, the pressure wave 114, and the surface of the eye 118 have been simplified for clarity. Configurations of the apparatus and/or the laser source 102, the treatment laser beam 104, the eye 106, the group of cells 108, the bubbles 110, the rupture 112 of the bubbles 110, the pressure wave 114, and the surface of the eye 118 are not limited to the configurations illustrated in diagram 100.

Current methods for measuring the vibration of the surface of the eye to determine cell damage rely on piezoelectric sensors mounted to the surface of the eye via a contact lens apparatus. The accuracy of these measurements by piezoelectric sensors may be limited because of the size of the contact apparatus. The contact apparatus that is typically attached to the eye may be about 1 cm in diameter, which may leave the instrument susceptible to interference. As a pressure wave moves through the vitreous humor, it may reflect from the retina walls leading to positive and negative interference with the pressure wave in varying amounts across the surface of the eye. This interference may result in a signal strength of the piezoelectric sensors that may be slightly above the noise level. In contrast, a laser Doppler vibrometer may allow vibrations at the surface of the eye to be detected using a smaller spot size. Because the spot size of laser vibrometry may be smaller than the wavelength of the pressure wave, improved spectral and spatial resolution may be achieved compared to piezoelectric sensing. Increased sensitivity may also be achieved. Thus, the enhanced quality of the received signal may provide simpler implementation for ophthalmologists and improved patient outcomes.

Figure 2:
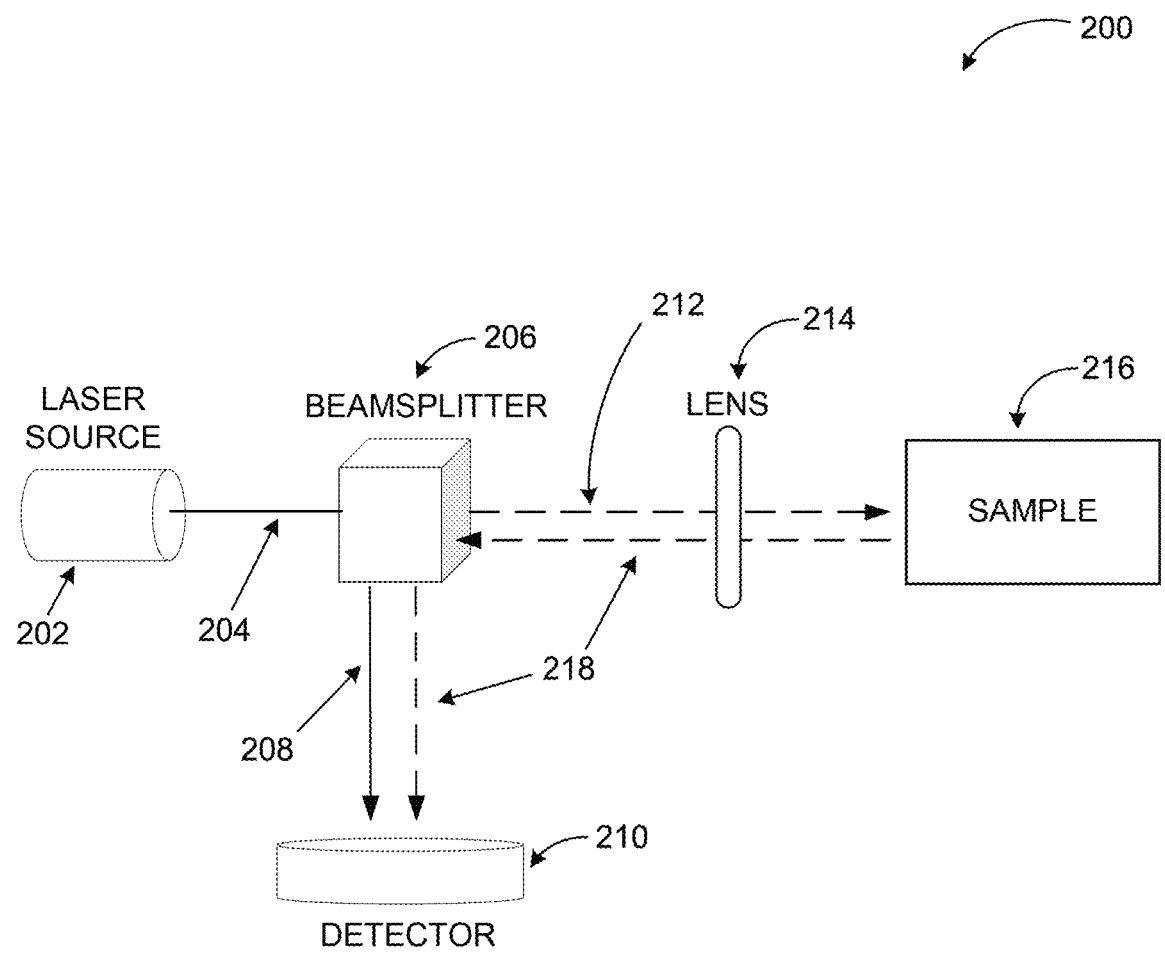
FIG. 2 illustrates an example laser Doppler vibrometer configured to measure vibrations at a surface of a sample.

FIG. 2 illustrates an example laser Doppler vibrometer configured to measure vibrations at a surface of a sample, arranged in accordance with at least some embodiments described herein.

As shown in diagram 200, a laser source 202 may be configured to generate a probe laser beam 204. In some examples, the laser source 202 may be a semiconductor laser diode, a super-luminescent laser diode, a chemical laser, a gas laser, a solid-state laser, and/or an optical fiber laser. The probe laser beam 204 may be directed towards a beam splitter 206 that splits the probe laser beam 204 into a first beam 208 and a second beam 212. The beam splitter 206 may be a dichroic beam splitter comprised of a cube with at least one mirrored face, for example. The first beam 208 may be a reference beam that is directed along a first optical path towards a detector 210. The second beam 212 may be a sample beam directed along a second optical path towards a surface of a sample 216. The second optical path may be oriented such that the second beam 212 may be presented normal to the surface of the sample 216 or may be presented to reflect light at an angle from the surface of sample 216. The second beam 212 may pass through a lens 214 configured to direct the second beam 212 towards the surface of the sample 216 and may be reflected back from the surface of the sample 216 creating a reflected beam 218.

The surface of sample 216 may be stationary or may be oscillating at the time the second beam 212 is reflected. If the surface of the sample 216 is oscillating at the time the second beam 212 encounters the surface, the second beam 212 may undergo a Doppler shift causing the reflected beam 218 to have a different frequency than the second beam 212. The Doppler shift may result in the reflected beam 218 interfering with the first beam 208. The reflected beam 218 may be directed to pass back through the lens 214 and into the beam splitter 206. The beam splitter may then direct the reflected beam 218 towards the detector 210. If the second beam 212 is presented to reflect light at an angle, the laser Doppler vibrometer may include one or more optical elements configured to collect the reflected beam 218 such that the detector 210 is able to detect the reflected beam. The detector 210 may include a photomultiplier, a photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, a quantum dot photoconductor, or comparable devices.

The detector 210 may be configured to provide a first signal based the first beam 208 and a second signal based on the reflected beam 218 to a signal processing component, where the signal processing component may be integrated with the laser Doppler vibrometer or may be a separate apparatus. A beat pattern signal may be derived from an interference between the first signal and the second signal, a frequency of the beat pattern signal may be isolated, and the Doppler shift may be determined from the frequency of the beat pattern signal. The frequency may be directly proportional to the velocity of and can be related to a motion (i.e., an oscillation or vibration) of the surface of the sample 216. In some embodiments, the laser Doppler vibrometer may optionally include an acousto-optic modulator (AOM) positioned along the first optical path. The AOM may be configured to shift the optical frequency of the first beam 208 slightly, such that both an amplitude and a direction of the motion of the surface of the sample 216 can be measured.

Figure 3:
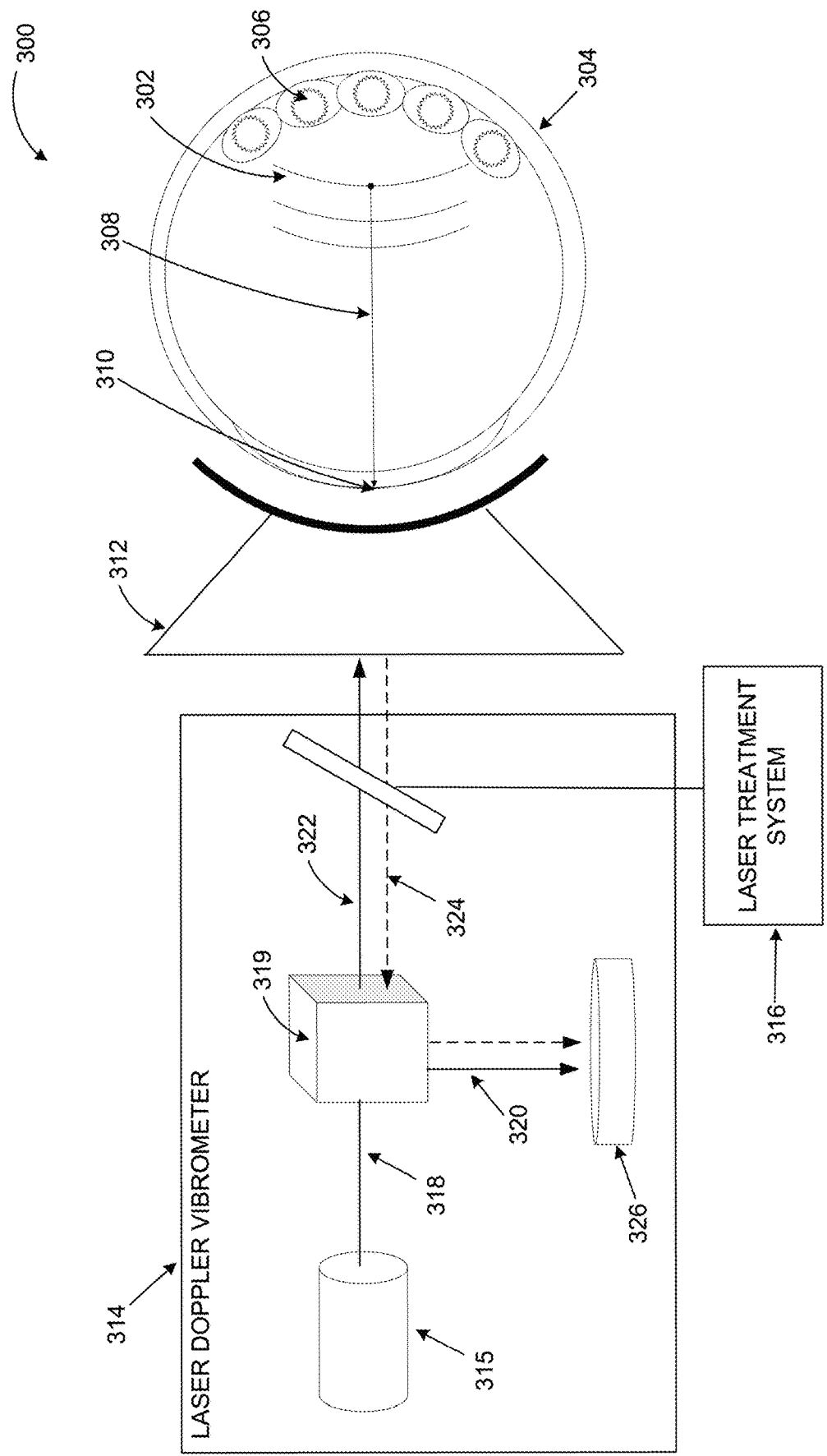
FIG. 3 illustrates an example system that includes a laser Doppler vibrometer configured to measure vibrations at a surface of an eye undergoing laser treatment in order to determine cell damage in a treatment area of the eye.

FIG. 3 illustrates an example system that includes a laser Doppler vibrometer configured to measure vibrations at a surface of an eye undergoing laser treatment in order to determine cell damage within a treatment area of the eye, arranged in accordance with at least some embodiments described herein.

As shown in diagram 300, pressure waves 302 may be created in the eye 304 during laser treatment. The pressure waves 302 may be created from the formation and/or rupture of bubbles 306 inside cells located within a treatment area of the eye 304 responsive to the direction of a laser treatment beam to the treatment area. The pressure waves 302 may travel through vitreous humor 308 and may encounter the eye's surface 310. This encounter may cause the eye's surface 310 to vibrate. During treatment, a contact apparatus 312 may be attached to the eye 304 and may also vibrate in tandem with the eye's surface 310. The contact apparatus 312 may include a contact lens, for example, positioned over the eye's surface.

As illustrated, in one embodiment, a laser Doppler vibrometer 314 may be configured to be a separate system or apparatus that operates in conjunction with a laser treatment system 316 to determine cell damage of the treated cells. The laser treatment system 316 may be configured to provide the laser treatment to the eye and may include, among other things, a treatment laser source configured to generate the treatment laser beam directed to the treatment area. The laser Doppler vibrometer 314 may be configured to measure eye surface vibration occurring at any time during the laser treatment. Measurements may be controlled by human control or may be configured for automatic operation, or may be directed by a remote controller through at least one network. In other embodiments, the laser Doppler vibrometer 314 may be integrated with the laser treatment system 316, where the treatment laser source of the laser treatment system 316 may be configured to generate and direct the treatment laser beam toward the treatment area and a probe laser source 315 of the laser Doppler vibrometer 314 may be configured to generate and direct a probe laser beam toward the surface of the eye in order to initiate laser Doppler vibrometry. In further embodiments, the laser Doppler vibrometer 314 may be integrated with the laser treatment system 316 such that the treatment laser beam and the probe laser beam are generated by a same laser source. In each of the above-described embodiments, the treatment laser beam and the probe laser beam may be generated at distinct wavelengths.

The probe laser source 315 of the laser Doppler vibrometer 314 may generate a probe laser beam 318 that may be split into a first beam 320 and a second beam 322 by a beam splitter 319. The probe laser beam 318 may be selected in a near infrared (NIR) spectral range such that the probe laser beam 318 may be directed continuously without harming the eye as it undergoes laser treatment. The power of the probe laser beam 318 may be less than 1 milliWatt (mW). The first beam 320 may be a reference beam that is directed along a first optical path towards a detector 326. The second beam 322 may be a sample beam that is directed along a second optical path towards the contact apparatus 312. A path length of the first optical path and the second optical path may vary from one another as long as the reference beam and a reflected sample beam from the contact apparatus 312 may be combined in such a way that they are still coherent. In other embodiments, the contact apparatus 312 may not be present, and the second beam 322 may be directed toward the eye's surface 310, such as a cornea of the eye. Reflective quality may be driven by a difference in optical index, and because a difference in optical index of the air-contact lens interface is similar to a difference in optical index of the air-cornea interface, directing the second beam 322 toward the cornea may produce similar reflection results as directing the second beam 322 toward the contact apparatus 312. In further embodiments, the second beam 322 may be directed toward a retina of the eye, however the retina may have stronger reflections from other interfaces, which may present additional challenges in isolating reflections from the second beam 322 from other reflections. The second beam 322 may be presented along the axis of treatment to the eye such that the second beam 322 is coaxial with the treatment laser beam. The axis of treatment may be normal to the surface of the contact apparatus 312. Alternatively, the second beam 322 may be presented to reflect light at an angle to the eye, or a diffuse scattering configuration may also be implemented.

The second beam 322 may be reflected from the surface of the contact apparatus 312 to generate a reflected beam 324. The surface of the contact apparatus 312 may be designed to optimize reflective properties. For example, a lens of the contact apparatus 312 may be coated with a reflective material in order to increase a reflection of the second beam 322 from the contact apparatus 312 as the reflected beam 324 in a manner that does not interfere with the treatment laser beam. The reflected beam 324 may have a different frequency than the second beam 322. This difference in frequency may result from a Doppler shift caused by the contact apparatus 312 vibrating in tandem with the eye's surface 310 when the second beam 322 is reflected, among other things. The Doppler shift may result in the reflected beam 324 interfering with the first beam 320. The reflected beam 324 may be directed back to the beam splitter 319, and the beam splitter 319 may then direct the reflected beam 324 towards the detector 326. If the second beam 322 is presented to reflect light at an angle to the eye, the laser Doppler vibrometer 314 may include one or more additional optical elements configured to collect the reflected beam 324 such that the detector 326 is able to detect the reflected beam 324.

The detector 326 may generate a first signal based on the first beam 320 and a second signal based on the reflected beam 324. In some embodiments, the detector 326 may be time-gated based on when the laser treatment beams are directed to the treatment area of the eye in order to increase sensitivity of detection. For example, the detector 326 may be prevented from detecting beams and/or generating signals based on detected beams during the time period in which the laser treatment beams are incident on the treatment area of the eye. Time-gating may be particularly effective if the probe laser beam 318 is being continuously directed toward the contact apparatus 312, and thus is necessarily overlapping with the direction of the treatment laser beam to the treatment area. Time-gating may allow the detector 326 to detect the first beam 320 and the reflected beam 324 without any interference from reflections of the laser treatment beam from the eye's surface 310 to increase sensitivity of the detection. In further embodiments, the laser Doppler vibrometer 314 may optionally include an acousto-optic modulator (AOM) positioned along the first optical path. The AOM may be configured to shift an optical frequency of the first beam 320 slightly, such that both an amplitude and a direction of a vibration of the eye's surface 310 can be measured.

The first and second signals may be received by a signal processing component, which may be integrated with the laser Doppler vibrometer 314, integrated with the laser treatment system 316, or a component of a separate signal processing apparatus. The signal processing component may be configured to derive a beat pattern signal from an interference between the first signal and the second signal. A frequency of the beat pattern signal may be isolated by performing a frequency-to-voltage conversion and/or a Fourier or comparable analysis.

Frequency-to-voltage conversion may be performed by an electronic circuit comprising discrete components or integrated circuits such as a signal processor or an application specific integrated circuit (ASIC). In frequency-to-voltage conversion, a periodic (e.g., sinusoidal) input frequency may be converted to a proportional voltage (or current). Example discrete component circuits may employ operational amplifiers and resistor-capacitor (RC) networks. An example circuit may charge a capacitor to a certain level. The capacitor may discharge into an integrator or a low pass circuit. The charge-discharge may be repeated for each cycle of the input waveform. A precision switch and/or a monostable multi-vibrator may generate a pulse of a specific amplitude proportional to the frequency of the input waveform. The output may further be averaged and used as DC output indicating the input frequency.

Fourier analysis employs approximated sums to represent periodic (e.g., sinusoidal) functions and is used to transform time domain signals to frequency domain signals. In the example scenarios discussed herein, Fourier analysis may be used as an example technique for signal processing that enables decomposition of a function, such as the beat pattern signal, into oscillatory components, such as the frequency of the beat pattern signal.

The frequency of the beat pattern signal may be directly proportional to the velocity of and can be related to a motion, such as the vibration of the eye's surface 310. Thus, the signal processing component may be configured to determine the Doppler shift from the frequency of the beat pattern signal and infer damage to one or more the cells within the treatment area of the eye in response to a determination that the Doppler shift is above a particular threshold frequency. The damage to the cells may include cell lysis, a rupture of cell membranes, scarring, and/or photocoagulation, among other examples. In some embodiments, the signal processing component may be configured to transmit a signal to the laser treatment system 316 to cease treatment (i.e., cease generation and direction of the treatment laser beam to the treatment area) in response to determining that the Doppler shift is above the particular threshold frequency, which is indicative of damage to the cells in the eye.

In an example scenario, a probe laser beam for detection of pressure waves may have a wavelength of 650 nm in order to distinguish the probe laser beam from a green treatment laser beam. The probe laser beam may be split by a beam splitter such that a first, reference beam is directed toward a detector and a second, sample beam may be directed toward a patient's eye. The second, sample beam may be presented along the axis of treatment to the eye (i.e., coaxial to a third optical path along which the treatment laser beam is directed) or may be presented to reflect light at an angle to the eye, or a diffuse scattering configuration may also be implemented. Upon contacting the surface of the eye or a contact apparatus, the second, sample beam may be reflected to create a reflected beam. If the surface of the eye is vibrating at the time of the encounter, a Doppler shift may occur causing the reflected beam to have a different frequency than the second, sample beam and the reflected beam to interfere with the first, reference beam. The reflected beam may be captured by beam splitter and directed towards the detector to compare the first, reference beam and the reflected beam. Signals based on the first, reference beam and the reflected beam may be analyzed by a signal processing component to determine if damage has occurred.

In other embodiments, instead of determining a Doppler shift from a frequency of the beat pattern signal derived from an interference between the first signal based on the first beam 320 (i.e., the reference beam) and the second signal based on the reflected beam 324, the Doppler shift may be determined using amplitude modulation. In such a configuration, the first beam 320 that is used as the reference beam would no longer be needed. However, the Doppler shift may be impacted by global displacement of the probe laser source 315, the detector 326 and the eye's surface 310, and would require very sensitive phase shift detection.

Embodiments as described herein are not limited to the context of an eye undergoing laser treatment. Similar embodiments may be used to monitor other areas of the body undergoing laser treatment, such as the nails or skin, among other examples.

Figure 4:
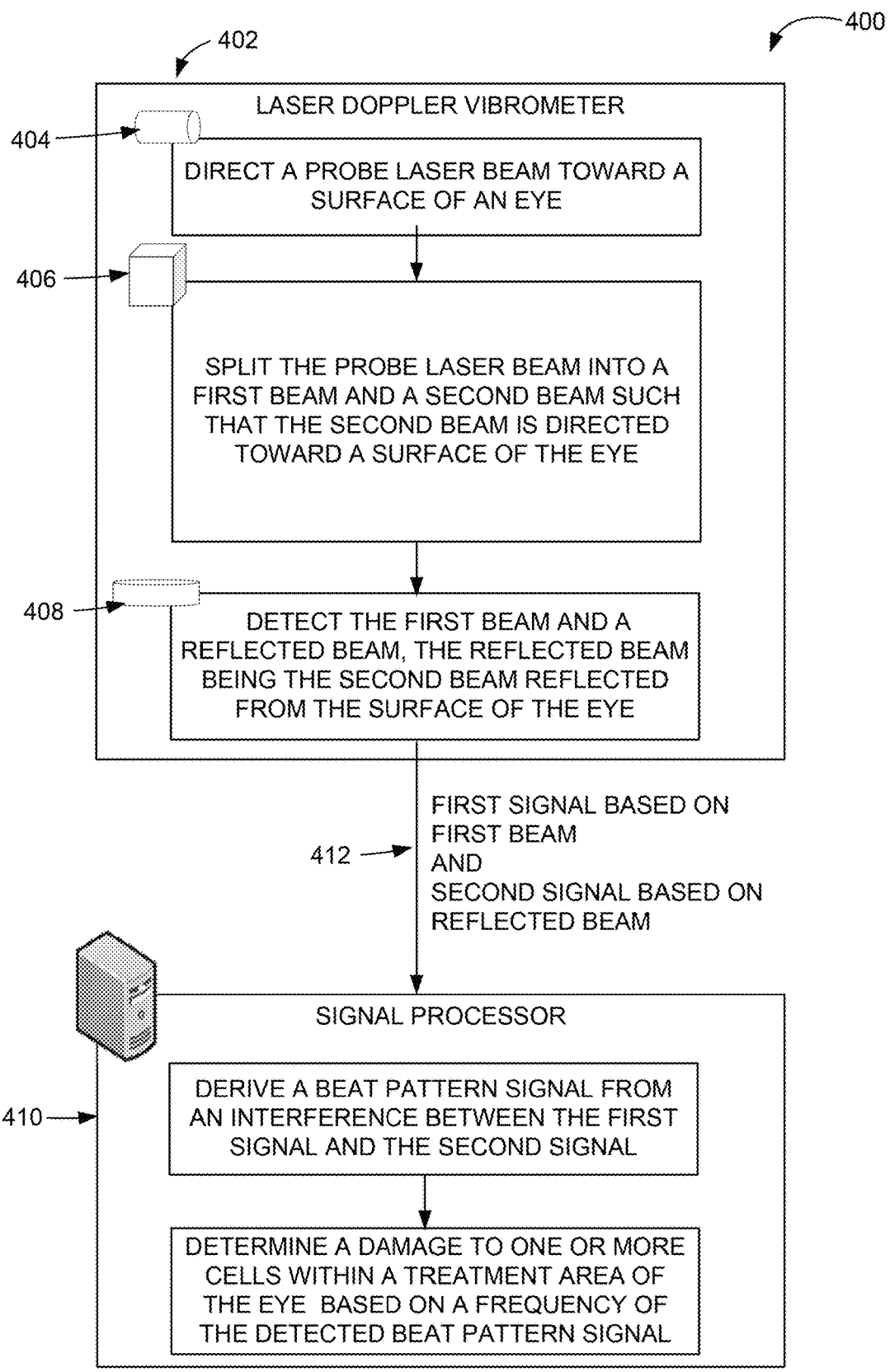
FIG. 4 includes a conceptual illustration of a system and a method to determine cell damage within an eye undergoing laser treatment.

FIG. 4 includes a conceptual illustration of a system and a method to determine cell damage within an eye undergoing laser treatment, arranged in accordance with at least some embodiments described herein.

As shown in diagram 400, an example system may include a laser Doppler vibrometer 402. The laser Doppler vibrometer 402 may include a laser source 404, a beam splitter 406, and a detector 408 among other things. The system may also include a signal processor 410. The signal processor 410 may be a computing device (e.g., a server, a desktop computer, a mobile computer, a special purpose computing device, or even a component level processor) configured to process signals from the laser Doppler vibrometer 402.

Example methods may include one or more operations, functions or actions as illustrated. The laser source 404 may be configured to, "DIRECT A PROBE LASER BEAM TOWARD A SURFACE OF AN EYE," among other things. The probe laser beam may be of any wavelength or amplitude, and may be distinct from a wavelength or amplitude of a treatment laser beam directed to a treatment area of the eye. Subsequently, the beam splitter 406 may be configured to, "SPLIT THE PROBE LASER BEAM INTO A FIRST BEAM AND A SECOND BEAM SUCH THAT THE SECOND BEAM IS DIRECTED TOWARD A SURFACE OF THE EYE." The first beam may be a reference beam that is directed along a first optical path towards the detector 408. The second beam may be a sample beam that is directed along a second optical path towards the surface of the eye, and may be reflected back from the surface of the eye creating a reflected beam.

The detector 408 may then be configured to, "DETECT THE FIRST BEAM AND A REFLECTED BEAM, THE REFLECTED BEAM BEING THE SECOND BEAM REFLECTED FROM THE SURFACE OF THE EYE." The detector 408 may be configured to generate a first signal based on the first beam and a second signal based on the reflected beam to be sent to the signal processor 410 as depicted by arrow 412.

Upon receiving the first signal and the second signal, the signal processor 410 may be configured to, "DERIVE A BEAT PATTERN SIGNAL FROM AN INTERFERENCE BETWEEN THE FIRST SIGNAL AND THE SECOND SIGNAL." The beat pattern signal may be in the form of:

$$I(t) = I_1 + I_2 + 2\text{SQRT}(I_1 I_2)\cos(2\pi(\Delta v)t + \Delta\varphi),$$

where $I_1$ is the intensity of the first signal based on first beam, $I_2$ is the intensity of the second signal based on the reflected beam, $\Delta v$ is the frequency difference between the first beam and the reflected beam, and $\Delta\varphi$ is a phase difference between the first signal and the second signal. The frequency may be directly proportional to the velocity of and can be related to a motion (i.e., a vibration) of the surface of the eye. A frequency-to-voltage conversion may be performed to isolate the frequency from the beat pattern signal. Additionally or alternatively, a Fourier or comparable analysis may be performed to isolate the frequency from the beat pattern signal.

Once the signal processor 410 has derived the beat pattern signal, it may also, "DETERMINE A DAMAGE TO ONE OR MORE CELLS WITHIN A TREATMENT AREA OF THE EYE BASED ON A FREQUENCY OF THE DETECTED BEAT PATTERN SIGNAL." This operation may include determining a Doppler shift from the frequency of the beat pattern signal and inferring damage to cells within a treatment area (i.e., an area undergoing laser treatment) of the eye in response to a determination that the Doppler shift is above a particular threshold frequency. In response to determining that the Doppler shift is above the particular threshold frequency, indicative of the damage to the cells, the signal processor 410 may be further configured to send a signal to a laser treatment system to cease treatment. Components of FIG. 4, such as the laser Doppler vibrometer 402, the laser source 404, the beam splitter 406, the detector 408, and/or the signal processor 410, are not limited to performing the actions, operations, or functions described in FIG. 4.

Figure 5:
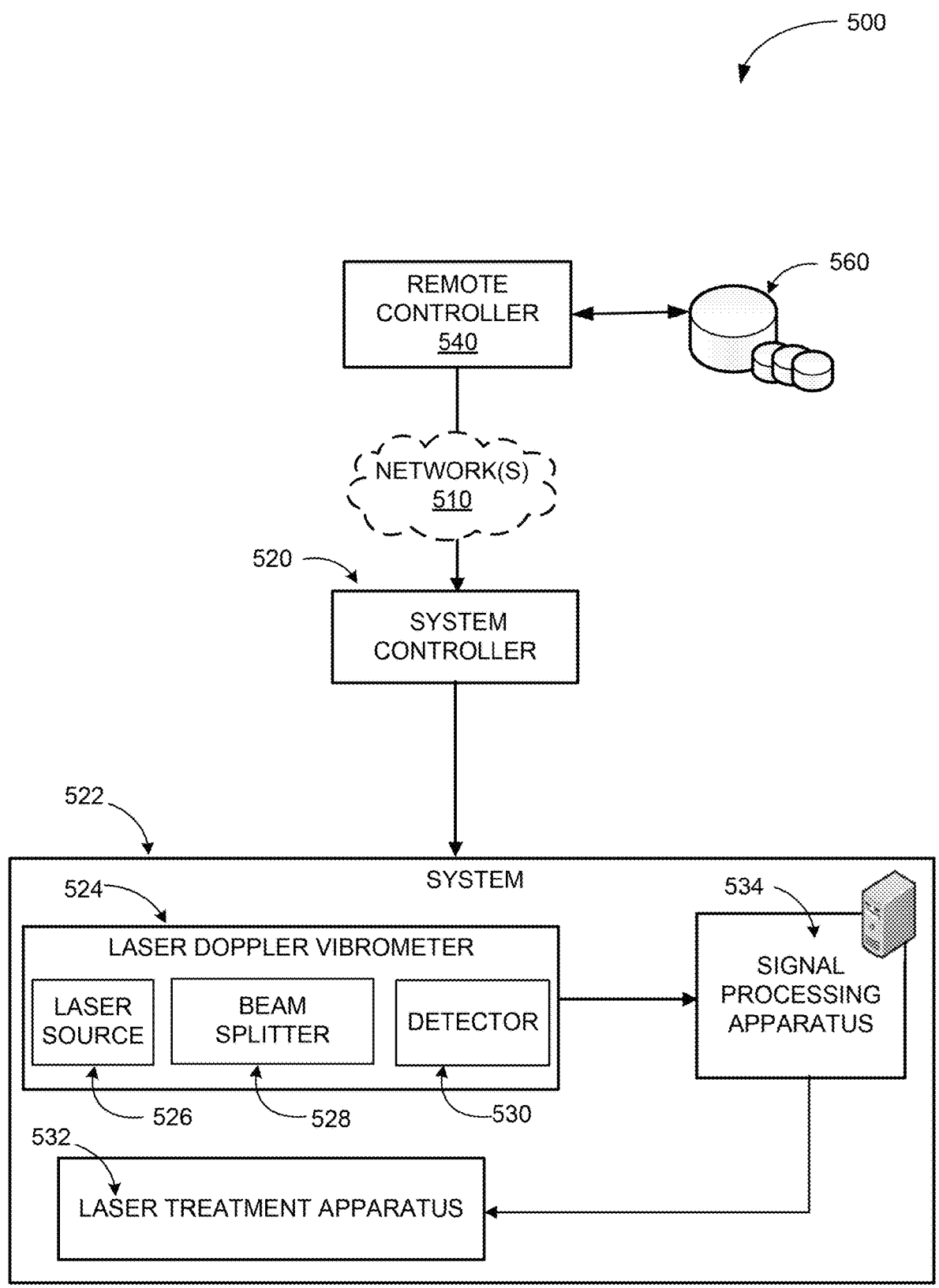
FIG. 5 illustrates major components of an example system configured to determine cell damage within an eye undergoing laser treatment.

FIG. 5 illustrates major components of an example system configured to determine cell damage within an eye undergoing laser treatment, arranged in accordance with at least some embodiments described herein.

As shown in diagram 500, a system 522 may be governed by a system controller 520. The system 522 may be a laser treatment system designed to remove diseased tissue in an eye, for example. The system controller 520 may be managed manually through a variety of inputs, may operate automatically after receiving one or more instructions, or may be operated independently by software. The system controller 520 may also be partially or entirely managed by a remote controller 540, for example, via network 510. The remote controller 540 may be managed manually through a variety of inputs, may operate automatically after receiving one or more instructions, or may be operated independently by software. Data associated with controlling the different processes of measuring eye surface vibration by laser Doppler vibrometry to determine cell damage may be stored at and/or received from data stores 560.

The system 522 may include a laser Doppler vibrometer 524, a signal processing apparatus 534, and a laser treatment apparatus 532. The laser treatment apparatus 532 may be configured to provide laser treatment to the eye by directing a treatment laser beam to a treatment area of the eye. The laser Doppler vibrometer 524 may include a laser source 526, a beam splitter 528, and a detector 530. In some examples, the laser source 526 may be a semiconductor laser diode, a super-luminescent laser diode, a chemical laser, a gas laser, a solid-state laser, and/or an optical fiber laser. The laser source 526 may be configured to direct a probe laser beam towards a surface of an eye, and the beam splitter 528 may be configured to split the probe laser beam into a first beam and a second beam. The beam splitter 528 may be a dichroic beam splitter comprised of a cube with at least one mirrored face, for example. The first beam may be a reference beam directed toward the detector and, the second beam may be a sample beam directed toward the surface of the eye. The detector 530 may be configured to detect the first beam and a reflected beam, the reflected beam being the second beam reflected from the surface of the eye. The detector 530 may include a photomultiplier, a photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, a quantum dot photoconductor, or comparable devices. The laser treatment apparatus 532 may operate independently from the laser Doppler vibrometer 524 or, in other embodiments, may be integrated with the laser Doppler vibrometer 524.

The system controller 520 may be configured to instruct the laser Doppler vibrometer 524 to transmit the first signal and the second signal to the signal processing apparatus 534. The signal processing apparatus 534 may be a computing device (e.g., a server, a desktop computer, a mobile computer, a special purpose computing device, or even a component level processor) configured to receive a first signal based on the first beam and a second signal based on the reflected beam from the laser Doppler vibrometer 524. The signal processing apparatus 534 may be configured to derive a beat pattern signal from an interference between the first and second signal, and may isolate a frequency of the beat pattern signal via a frequency-to-voltage conversion and/or a Fourier or comparable analysis. The signal processing apparatus 534 may be further configured to determine a damage to one or more cells within the treatment area of the eye based on the frequency of the detected beat pattern signal. For example, the signal processing apparatus 534 may determine a Doppler shift from the frequency of the beat pattern signal and infer the damage to the cells in response to a determination that the Doppler shift is above a particular threshold frequency. The system controller 520 may be configured to instruct the laser treatment apparatus 532 to cease direction of the treatment laser beam to the treatment area of the eye in response to the determination of the damage to the cells by the signal processing apparatus 534.

The examples provided in FIGS. 1 through 5 are illustrated with specific systems, devices, applications, and scenarios. Embodiments are not limited to environments according to these examples. Detection of eye surface vibration through laser Doppler vibrometry to determine cell damage may be implemented in environments employing fewer or additional systems, devices, applications, and scenarios. Furthermore, the example systems, devices, applications, and scenarios shown in FIGS. 1 through 5 may be implemented in a similar manner with other user interface or action flow sequences using the principles described herein.

Figure 6:
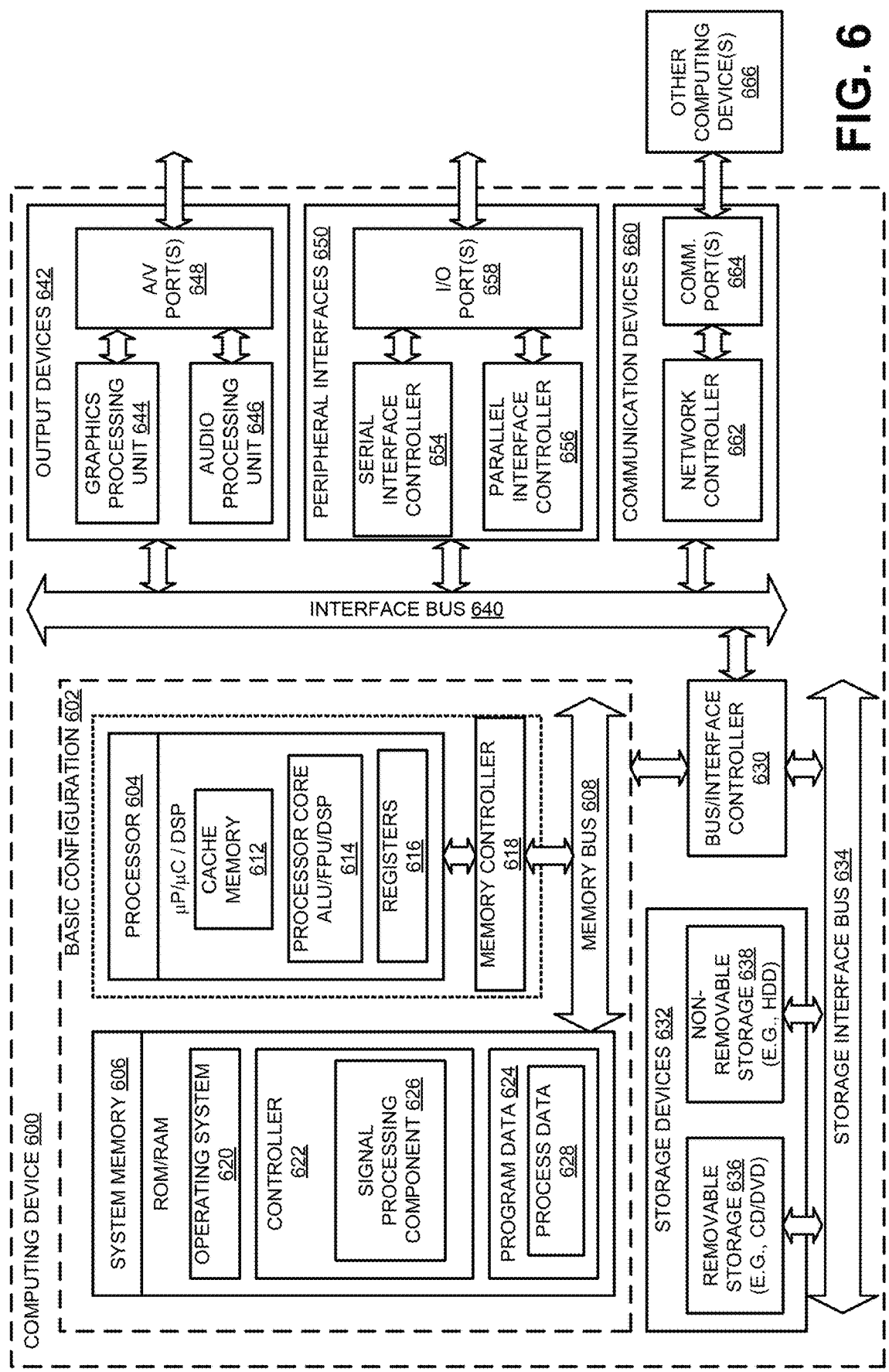
FIG. 6 illustrates a computing device, which may be communicatively coupled to and used in conjunction with a laser Doppler vibrometer to determine cell damage within an eye undergoing laser treatment.

FIG. 6 illustrates a computing device, which may be communicatively coupled to and used in conjunction with a laser Doppler vibrometer to determine cell damage within an eye undergoing laser treatment, arranged in accordance with at least some embodiments described herein.

In an example basic configuration 602, the computing device 600 may include one or more processors 604 and a system memory 606. A memory bus 608 may be used to communicate between the processor 604 and the system memory 606. The basic configuration 602 is illustrated in FIG. 6 by those components within the inner dashed line.

Depending on the desired configuration, the processor 604 may be of any type, including but not limited to a microprocessor (µP), a microcontroller (µC), a digital signal processor (DSP), or any combination thereof. The processor 604 may include one or more levels of caching, such as a cache memory 612, a processor core 614, and registers 616. The example processor core 614 may include an arithmetic logic unit (ALU), a floating point unit (FPU), a digital signal processing core (DSP Core), or any combination thereof. An example memory controller 618 may also be used with the processor 604, or in some implementations, the memory controller 618 may be an internal part of the processor 604.

Depending on the desired configuration, the system memory 606 may be of any type including but not limited to volatile memory (such as RAM), non-volatile memory (such as ROM, flash memory, etc.) or any combination thereof. The system memory 606 may include an operating system 620, a controller 622, and program data 624. The controller 622 may include a signal processing unit 626. The controller 622 may be configured to send and/or receive signals from components associated with a laser treatment system and/or a laser Doppler vibrometer. The signal processing unit 626 may be configured to receive a first signal and a second signal, derive a beat pattern signal from an interference between the first signal and the second signal, and determine damage to one or more cells within a treatment area of the eye based on a frequency of the beat pattern signal. The program data 624 may include, among other data, process data 628 or the like, as described herein.

The computing device 600 may have additional features or functionality, and additional interfaces to facilitate communications between the basic configuration 602 and any desired devices and interfaces. For example, a bus/interface controller 630 may be used to facilitate communications between the basic configuration 602 and one or more data storage devices 632 via a storage interface bus 634. The data storage devices 632 may be one or more removable storage devices 636, one or more non-removable storage devices 638, or a combination thereof. Examples of the removable storage and the non-removable storage devices include magnetic disk devices such as flexible disk drives and hard-disk drives (HDDs), optical disk drives such as compact disc (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer readable instructions, data structures, program modules, or other data.

The system memory 606, the removable storage devices 636 and the non-removable storage devices 638 are examples of computer storage media. Computer storage media includes, but is not limited to, RAM, ROM, EEPROM, flash memory or other memory technology, CD-ROM, digital versatile disks (DVDs), solid state drives (SSDs), or other optical storage, magnetic cassettes, magnetic tape, magnetic disk storage or other magnetic storage devices, or any other medium which may be used to store the desired information and which may be accessed by the computing device 600. Any such computer storage media may be part of the computing device 600.

The computing device 600 may also include an interface bus 640 for facilitating communication from various interface devices (e.g., one or more output devices 642, one or more peripheral interfaces 650, and one or more communication devices 660) to the basic configuration 602 via the bus/interface controller 630. Some of the example output devices 642 include a graphics processing unit 644 and an audio processing unit 646, which may be configured to communicate to various external devices such as a display or speakers via one or more A/V ports 648. One or more example peripheral interfaces 650 may include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 660 includes a network controller 662, which may be arranged to facilitate communications with one or more other computing devices 666 over a network communication link via one or more communication ports 664. The one or more other computing devices 666 may include servers at a datacenter, customer equipment, and comparable devices.

The network communication link may be one example of a communication media. Communication media may be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 600 may be implemented as a part of a general purpose or specialized server, mainframe, or similar computer that includes any of the above functions. The computing device 600 may also be implemented as a personal computer including both laptop computer and non-laptop computer configurations.

Figure 7:
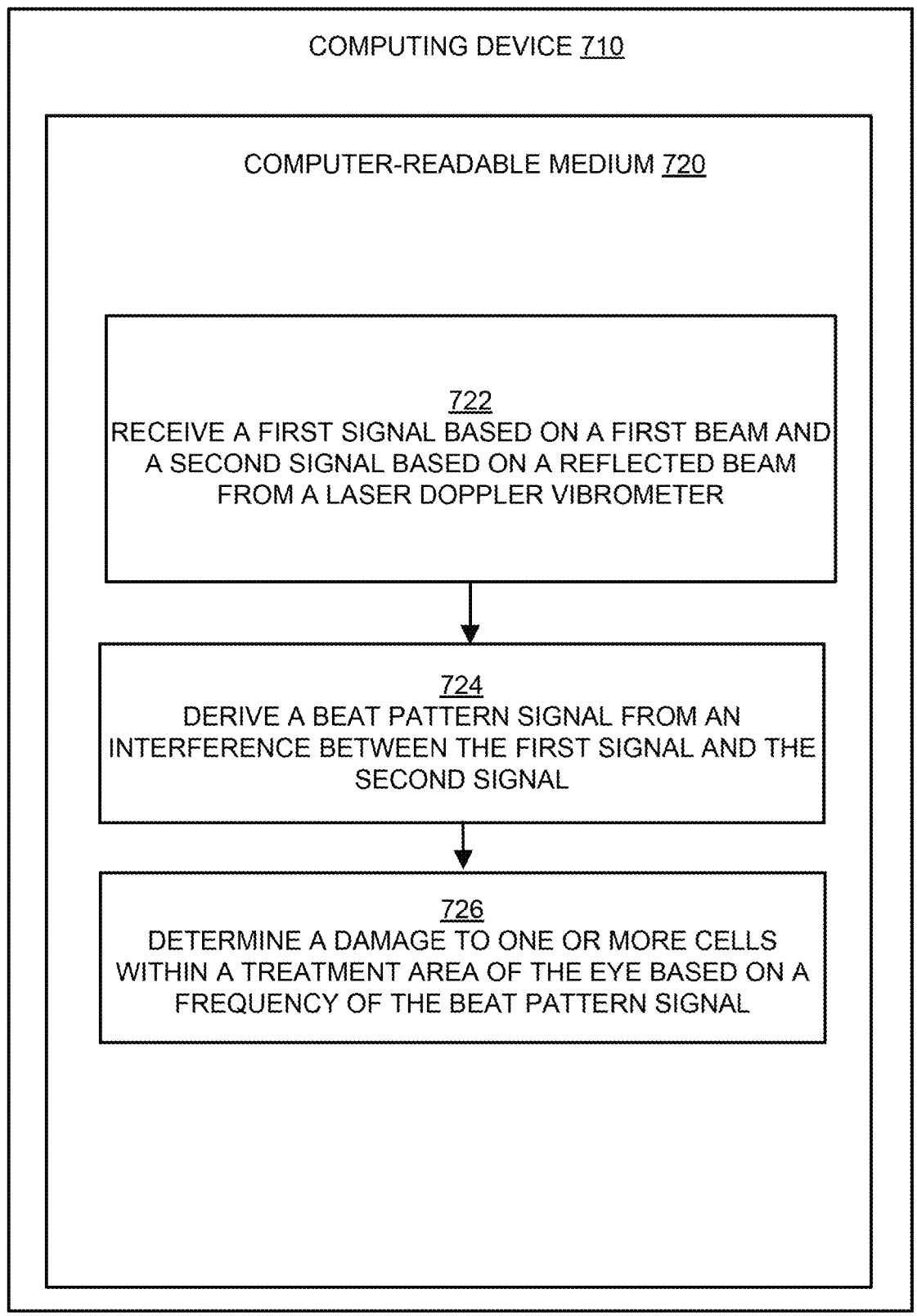
FIG. 7 is a flow diagram illustrating an example method to determine cell damage within an eye undergoing laser treatment that may be performed by a laser Doppler vibrometer in conjunction with a computing device such as the computing device in FIG. 6.

FIG. 7 is a flow diagram illustrating an example method to determine cell damage within an eye undergoing laser treatment that may be performed by a laser Doppler vibrometer in conjunction with a computing device such as the computing device in FIG. 6, arranged in accordance with at least some embodiments described herein.

Example methods may include one or more operations, functions or actions as illustrated by one or more of blocks 722, 724, and/or 726, and may in some embodiments be performed by a computing device such as the computing device 710 in FIG. 7. The operations described in the blocks 722-726 may also be stored as computer-executable instructions in a computer-readable medium such as a computer-readable medium 720 of a computing device 710.

An example process to determine cell damage within an eye undergoing laser treatment may begin with block 722, "RECEIVE A FIRST SIGNAL BASED ON A FIRST BEAM AND A SECOND SIGNAL BASED ON A REFLECTED BEAM FROM A LASER DOPPLER VIBROMETER", where a first signal and a second signal may be received from a laser Doppler vibrometer. For example, a probe laser source of the laser Doppler vibrometer may be configured to direct a probe laser beam towards a surface of an eye. A beam splitter of the laser Doppler vibrometer may be configured to split the probe beam into a first, reference beam and the second, sample beam. The first, reference beam may be directed along a first optical path toward a detector of the laser Doppler vibrometer. The second, sample beam may be directed along the second optical path toward the surface of the eye causing the second beam to be reflected from the surface of the eye, which creates a reflected beam received at the beam splitter and directed to the detector. The detector may derive the first signal from the first, reference beam and the second signal from the reflected beam.

Block 722 may be followed by block 724, "DERIVE A BEAT PATTERN SIGNAL FROM AN INTERFERENCE BETWEEN THE FIRST SIGNAL AND THE SECOND SIGNAL", where a beat pattern signal may be derived from an interference between the first and second signal. A frequency of the beat pattern signal may be isolated from the beat pattern signal. The frequency may be isolated through a frequency-to-voltage conversion and/or a Fourier or comparable analysis.

Block 724 may be followed by block 726, "DETERMINE A DAMAGE TO ONE OR MORE CELLS WITHIN A TREATMENT AREA OF THE EYE BASED ON A FREQUENCY OF THE BEAT PATTERN SIGNAL", where a Doppler shift may be determined from the frequency of the beat pattern signal. In response to a determination that the Doppler shift is above a particular threshold frequency, damage to the cells within the treatment area may be inferred. The damage to the cells may include cell lysis, a rupture of cell membranes, scarring, and/or photocoagulation, among other examples.

The operations included in process 700 are for illustration purposes. Determination of cell damage within an eye undergoing laser treatment may be implemented by similar processes with fewer or additional steps, as well as in different order of operations using the principles described herein. The operations described herein may be executed by one or more processors operated on one or more computing devices, one or more processor cores, specialized processing devices, and/or general purpose processors, among other examples.

FIG. 8 illustrates a block diagram of an example computer program product, some of which are arranged in accordance with at least some embodiments described herein.

In some examples, as shown in FIG. 8, a computer program product 800 may include a signal bearing medium 802 that may also include one or more machine readable instructions 804 that, when executed by, for example, a processor may provide the functionality described herein. Thus, for example, referring to the processor 604 in FIG. 6, the controller 622 may undertake one or more of the tasks shown in FIG. 8 in response to the instructions 804 conveyed to the processor 604 by the signal bearing medium 802 to perform actions associated with measuring eye surface vibration through laser Doppler vibrometry to determine cell damage as described herein. Some of those instructions 804 may include, for example, one or more instructions to receive a first signal based on a first beam and a second signal based on a reflected beam from a laser Doppler vibrometer; derive a beat pattern signal from an interference between the first signal and the second signal; and determine a damage to one or more cells within a treatment area of the eye based on a frequency of the beat pattern signal according to some embodiments described herein.

In some implementations, the signal bearing medium 802 depicted in FIG. 8 may encompass computer-readable medium 806, such as, but not limited to, a hard disk drive (HDD), a solid state drive (SSD), a compact disc (CD), a digital versatile disk (DVD), a digital tape, memory, etc. In some implementations, the signal bearing medium 802 may encompass recordable medium 808, such as, but not limited to, memory, read/write (R/W) CDs, R/W DVDs, etc. In some implementations, the signal bearing medium 802 may encompass communications medium 810, such as, but not limited to, a digital and/or an analog communication medium (e.g., a fiber optic cable, a waveguide, a wired communication link, a wireless communication link, etc.). Thus, for example, the computer program product 800 may be conveyed to one or more modules of the processor 604 by an RF signal bearing medium, where the signal bearing medium 802 is conveyed by the communications medium 810 (e.g., a wireless communications medium conforming with the IEEE 802.11 standard).

According to some examples a method to determine cell damage within an eye undergoing laser treatment may comprise directing a probe laser beam toward a surface of the eye by splitting the probe laser beam into a first beam and a second beam and directing the second beam toward the surface of the eye. The method may further comprise detecting a beat pattern signal between the first beam and a reflected beam, the reflected beam being the second beam reflected from the surface of the eye and determining a damage to one or more cells within a treatment area of the eye based on a frequency of the beat pattern signal.

According to further examples, a treatment laser beam may be directed to the treatment area of the eye prior to or while the probe laser beam is directed toward the surface of the eye, and in response to determining the damage to the one or more cells, direction of the treatment laser beam to the treatment area of the eye may be ceased. In further examples, directing the probe laser beam toward the surface of the eye may comprise one of directing the probe laser beam toward a cornea of the eye or directing the probe laser beam toward a contact lens positioned on the cornea of the eye. In other examples, the methods may further include directing the first beam along a first optical path away from the surface of the eye and toward a detector such that the detector is configured to detect the first beam. In further examples, directing the second beam towards the surface of the eye may comprise directing the second beam along a second optical path normal to the surface of the eye or directing the second beam along a second optical path at an angle to the surface of the eye. In still other examples, the method may also comprise isolating the frequency of the beat pattern signal, performing a frequency-to-voltage conversion to isolate the frequency of the beat pattern signal, or performing a Fourier analysis to isolate the frequency of the beat pattern signal. In further examples, determining the damage to the one or more cells based on the frequency of the beat pattern signal may comprise determining a Doppler shift from the frequency of the beat pattern signal and inferring the damage to the one or more cells in response to a determination that the Doppler shift is above a particular threshold frequency.

According to some embodiments, a laser Doppler vibrometer may be comprised of a probe laser source configured to direct a probe laser beam toward a surface of an eye, a beam splitter positioned between the probe laser source and the eye and configured to split the probe laser beam into a first beam and a second beam such that the second beam is directed toward the surface of the eye, and a detector. The detector may be configured to detect the first beam and a reflected beam, the reflected beam being the second beam reflected from the surface of the eye and provide a first signal based on the first beam and a second signal based on the reflected beam to a signal processing apparatus, wherein the signal processing apparatus is configured to derive a beat pattern signal from an interference between the first signal and the second signal in order to determine a damage to one or more cells within a treatment area of the eye based on a frequency of the beat pattern signal.

In other embodiments, the signal processing apparatus may be configured to determine the damage to the one or more cells based on the frequency of the beat pattern signal by determining a Doppler shift from the frequency of the beat pattern signal and inferring the damage to the one or more cells in response to a determination that the Doppler shift is above a particular threshold frequency. In further embodiments, the signal processing apparatus may be further configured to instruct a treatment laser source to cease direction of a treatment beam to the treatment area of the eye in response to the determination that the Doppler shift is above the particular threshold frequency. In other embodiments, the treatment laser source may be a component of the laser Doppler vibrometer or the probe laser source and the treatment laser source may be a single laser source, or the treatment laser source may be a component of a laser treatment system communicatively coupled to the laser Doppler vibrometer. In further embodiments, the surface of the eye may include a cornea of the eye or a contact lens positioned on the cornea of the eye.

In other embodiments, the probe laser source may be a semiconductor laser diode, a super-luminescent laser diode, a chemical laser, a gas laser, a solid-state laser, and/or an optical fiber laser. In other embodiments, the detector may be one of a photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, and a quantum dot photoconductor. In other embodiments, the first beam may be directed along a first optical path away from the surface of the eye and toward the detector configured to detect the reference beam, and the laser Doppler vibrometer may further comprise an acousto-optic modulator (AOM) positioned along the first optical path. In further embodiments, the second beam may be directed along a second optical path normal to the surface of the eye, or the second optical path may be coaxial to a third optical path along which a treatment laser beam may be directed to a treatment area of the eye. In still further embodiments, the laser Doppler vibrometer may comprise one or more optical elements configured to collect the reflected beam such that the detector is able to detect the reflected beam.

According to some examples, a signal processing apparatus may be comprised of a communication interface configured to facilitate communication between the signal processing apparatus and a laser Doppler vibrometer. The laser Doppler vibrometer may be configured to direct a probe laser beam toward a surface of the eye by splitting the probe laser beam into a first beam and a second beam such that the second beam may be directed toward the surface of the eye, and detect the first beam and a reflected beam, the reflected beam being the second beam reflected from the surface of the eye. The signal processing apparatus may also be comprised of a processor coupled to the communication interface. The processor may be configured to receive, from the laser Doppler vibrometer through the communication interface, a first signal based on the first beam and a second signal based on the reflected beam, derive a beat pattern signal from an interference between the first signal and the second signal, and determine a damage to one or more cells within a treatment area of the eye on a frequency of the beat pattern signal.

In other examples, the processor may be further configured to isolate the frequency of the beat pattern signal, perform a frequency-to-voltage conversion to isolate the frequency of the beat pattern signal, or perform a Fourier analysis to isolate the frequency of the beat pattern signal. In further examples, in order to determine the damage to the one or more cells based on the frequency of the beat pattern signal, the processor may be configured to determine a Doppler shift from the frequency of the beat pattern signal and infer the damage to the one or more cells in response to a determination that the Doppler shift is above a particular threshold frequency. In other examples, the processor may be further configured to instruct a treatment laser source to cease direction of a treatment beam to the treatment area of the eye in response to the determination that the Doppler shift is above the particular threshold frequency. In further examples, the treatment laser source may be a component of the laser Doppler vibrometer or a component of a laser treatment system.

According to some embodiments, a system to determine cell damage within an eye undergoing laser treatment may be comprised of a laser treatment system configured to direct a treatment laser beam to a treatment area of the eye and a laser Doppler vibrometer communicatively coupled to the treatment system. The laser Doppler vibrometer may be configured to direct a probe laser beam toward a surface of the eye by splitting the probe laser beam into a first beam and a second beam, directing the second beam toward the surface of the eye, and detect the first beam and a reflected beam, the reflected beam being the second beam reflected from the surface of the eye. The system may also comprise a signal processing apparatus communicatively coupled to the laser treatment system and the laser Doppler vibrometer. The signal processing apparatus may be configured to receive a first signal based on the first beam and a second signal based on the reflected beam, derive a beat pattern signal from an interference between the first signal and the second signal, and determine a damage to one or more cells within the treatment area of the eye based on a frequency of the beat pattern signal.

In other embodiments, the system may further comprise a controller communicatively coupled to and configured to control and coordinate one or more operations of the laser treatment system, the laser Doppler vibrometer, and the signal processing apparatus. In further embodiments, the controller may be configured to instruct the laser treatment system to cease direction of the treatment laser beam to the treatment area of the eye in response to the determination of the damage to the one or more cells by the signal processing apparatus. In other embodiments, the controller may be configured to instruct the laser Doppler vibrometer to transmit the first signal and the second signal to the signal processing apparatus. In further embodiments, a treatment laser source may be configured to emit the treatment laser beam and a probe laser source is configured to emit the probe laser beam. In other embodiments, the treatment laser source may be a component of the laser treatment system and the probe laser source is a component of the laser Doppler vibrometer or the treatment laser source and the probe laser source may be components of the laser Doppler vibrometer, or the treatment laser source and the probe laser source may be a single laser source.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for mainly hardware and/or firmware vehicle; if flexibility is paramount, the implementer may opt for mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs executing on one or more computers (e.g., as one or more programs executing on one or more computer systems), as one or more programs executing on one or more processors (e.g., as one or more programs executing on one or more microprocessors), as firmware, or as virtually any combination thereof, and that designing the circuitry and/or writing the code for the software and/or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a compact disc (CD), a digital versatile disk (DVD), a digital tape, a computer memory, a solid state drive (SSD), etc.; and a transmission type medium such as a digital and/or an analog communication medium (e.g., a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a data processing system may include one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors.

A data processing system may be implemented utilizing any suitable commercially available components, such as those found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method to determine cell damage within an eye undergoing laser treatment, the method comprising:
   directing a probe laser beam toward a surface of the eye by:
   splitting the probe laser beam into a first beam and a second beam; and
   directing the second beam toward the surface of the eye;
   detecting a beat pattern signal between the first beam and a reflected beam, the reflected beam being a reflected portion of the second beam that is reflected from the surface of the eye; and
   determining a damage to one or more cells within a treatment area of the eye based on a frequency of the detected beat pattern signal.

2. The method of claim 1, further comprising:
   directing a treatment laser beam to the treatment area of the eye prior to or while directing the probe laser beam toward the surface of the eye.

3. The method of claim 1, wherein directing the probe laser beam toward the surface of the eye comprises one of:
 directing the probe laser beam toward a cornea of the eye; or
 directing the probe laser beam toward a contact lens positioned on the cornea of the eye.

4. The method of claim 1, further comprising:
 directing the first beam along a first optical path away from the surface of the eye and toward a detector such that the detector is configured to detect the first beam; and
 directing the second beam along a second optical path normal or at an angle to the surface of the eye.

5. The method of claim 1, further comprising:
 isolating the frequency of the beat pattern signal through one or more of a frequency-to-voltage conversion or a Fourier analysis.

6. The method of claim 1, wherein determining the damage to the one or more cells within the treatment area of the eye based on the frequency of the detected beat pattern signal comprises:
 determining a Doppler shift from the frequency of the beat pattern signal; and
 identifying the damage to the one or more cells in response to a determination that the Doppler shift is above a particular threshold frequency.

7. A laser Doppler vibrometer, comprising:
 a probe laser source configured to direct a probe laser beam toward a surface of an eye;
 a beam splitter positioned between the probe laser source and the eye and configured to split the probe laser beam into a first beam and a second beam such that the second beam is directed toward the surface of the eye; and
 a detector configured to:
  detect the first beam and a reflected beam, the reflected beam being a reflected portion of the second beam that is reflected from the surface of the eye; and
  provide a first signal based on the first beam and a second signal based on the reflected beam to a signal processing apparatus for the signal processing apparatus to derive a beat pattern signal from an interference between the first signal and the second signal in order to determine a damage to one or more cells within a treatment area of the eye based on a frequency of the beat pattern signal.

8. The laser Doppler vibrometer of claim 7, wherein the signal processing apparatus is configured to determine the damage to the one or more cells within the treatment area of the eye based on the frequency of the beat pattern signal by:
 determination of a Doppler shift from the frequency of the beat pattern signal; and
 identification of the damage to the one or more cells in response to a determination that the Doppler shift is above a particular threshold frequency.

9. The laser Doppler vibrometer of claim 8, wherein
 the signal processing apparatus is further configured to instruct a treatment laser source to cease direction of a treatment beam to the treatment area of the eye in response to the determination that the Doppler shift is above the particular threshold frequency, and wherein the treatment laser source is a component of the laser Doppler vibrometer,
 the probe laser source and the treatment laser source are a single laser source, or
 the treatment laser source is a component of a laser treatment system communicatively coupled to the laser Doppler vibrometer.

10. The laser Doppler vibrometer of claim 7, wherein
 the probe laser source is one of a semiconductor laser diode, a super-luminescent laser diode, a chemical laser, a gas laser, a solid-state laser, and an optical fiber laser,
 the beam splitter is a dichroic beam splitter comprised of a cube with at least one mirrored face, and
 the detector is one of a photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, and a quantum dot photoconductor.

11. The laser Doppler vibrometer of claim 7, wherein the first beam is directed along a first optical path away from the surface of the eye and toward the detector configured to detect the first beam and the laser Doppler vibrometer further comprises an acousto-optic modulator (AOM) positioned along the first optical path.

12. The laser Doppler vibrometer of claim 7, wherein the second beam is directed along a second optical path normal to the surface of the eye and the second optical path is coaxial to a third optical path along which a treatment laser beam is directed to the treatment area of the eye.

13. The laser Doppler vibrometer of claim 7, wherein the second beam is directed along a second optical path at an angle to the surface of the eye and the laser Doppler vibrometer further comprises one or more optical elements configured to collect the reflected beam such that the detector is able to detect the reflected beam.

14. A signal processing apparatus, comprising:
 a communication interface configured to facilitate communication between the signal processing apparatus and a laser Doppler vibrometer, wherein the laser Doppler vibrometer is configured to direct a probe laser beam toward a surface of an eye by splitting the probe laser beam into a first beam and a second beam such that the second beam is directed toward the surface of the eye, and detect the first beam and a reflected beam, the reflected beam being a reflected portion of the second beam that is reflected from the surface of the eye; and
 a processor coupled to the communication interface, wherein the processor is configured to:
  receive, from the laser Doppler vibrometer through the communication interface, a first signal based on the first beam and a second signal based on the reflected beam;
  derive a beat pattern signal from an interference between the first signal and the second signal; and
  determine a damage to one or more cells within a treatment area of the eye based on a frequency of the beat pattern signal.

15. The signal processing apparatus of claim 14, wherein the processor is further configured to isolate the frequency of the beat pattern signal through one or more of a frequency-to-voltage conversion or a Fourier analysis.

16. The signal processing apparatus of claim 14, wherein, to determine the damage to the one or more cells within the treatment area of the eye based on the frequency of the beat pattern signal, the processor is configured to:
 determine a Doppler shift from the frequency of the beat pattern signal;

identify the damage to the one or more cells in response to a determination that the Doppler shift is above a particular threshold frequency; and instruct a treatment laser source to cease direction of a treatment beam to the treatment area of the eye in response to the determination that the Doppler shift is above the particular threshold frequency.

17. A system to determine cell damage within an eye undergoing laser treatment, the system comprising:

a laser treatment system configured to direct a treatment laser beam to a treatment area of the eye;

a laser Doppler vibrometer communicatively coupled to the laser treatment system, wherein the laser Doppler vibrometer is configured to:

direct a probe laser beam toward a surface of the eye by:

splitting the probe laser beam into a first beam and a second beam; and directing the second beam toward the surface of the eye; and detect the first beam and a reflected beam, the reflected beam being a reflected portion of the second beam that is reflected from the surface of the eye; and a signal processing apparatus communicatively coupled to the laser treatment system and the laser Doppler vibrometer, wherein the signal processing apparatus is configured to:

receive a first signal based on the first beam and a second signal based on the reflected beam;

derive a beat pattern signal from an interference between the first signal and the second signal; and determine a damage to one or more cells within the treatment area of the eye based on a frequency of the beat pattern signal.

18. The system of claim 17, wherein the system further comprises a controller communicatively coupled to and configured to control and coordinate one or more operations of the laser treatment system, the laser Doppler vibrometer, and the signal processing apparatus.

19. The system of claim 18, wherein the controller is configured to:

instruct the laser treatment system to cease direction of the treatment laser beam to the treatment area of the eye in response to a determination of the damage to the one or more cells within the treatment area of the eye by the signal processing apparatus; and instruct the laser Doppler vibrometer to transmit the first signal and the second signal to the signal processing apparatus.

20. The system of claim 17, wherein a treatment laser source and a probe laser source are components of the laser Doppler vibrometer.

* * * * *